United States Patent
Ottens et al.

(10) Patent No.: US 7,208,448 B2
(45) Date of Patent: Apr. 24, 2007

(54) IN AN AMINE OR NITRILE EMBEDDED PASSIVATED HYDROGENATION CATALYST

(75) Inventors: Thale Jacob Ottens, Laren (NL); Jacobus Van Den Berg, Voorthuizen (NL); Paul Van Poecke, Lochem (NL)

(73) Assignee: Akzo Nobel N.V., Arnhem (NL)

( * ) Notice: Subject to any disclaimer, the term of this patent is extended or adjusted under 35 U.S.C. 154(b) by 187 days.

(21) Appl. No.: 10/505,661

(22) PCT Filed: Mar. 13, 2003

(86) PCT No.: PCT/EP03/02637

§ 371 (c)(1),
(2), (4) Date: Sep. 14, 2004

(87) PCT Pub. No.: WO03/080243

PCT Pub. Date: Oct. 2, 2003

(65) Prior Publication Data
US 2005/0124833 A1 Jun. 9, 2005

(30) Foreign Application Priority Data
Mar. 25, 2002 (EP) .................................. 02076170

(51) Int. Cl.
*B01J 33/00* (2006.01)
*C07C 209/48* (2006.01)

(52) U.S. Cl. .................. 502/521; 502/500; 502/527.24; 564/490; 564/491; 564/492; 564/493

(58) Field of Classification Search ................ 502/500, 502/521, 527.24
See application file for complete search history.

(56) References Cited

U.S. PATENT DOCUMENTS

| | | | |
|---|---|---|---|
| 2,730,533 A | 1/1956 | Umhoefer | |
| 3,033,802 A | 5/1962 | Pedigo | |
| 4,086,275 A | 4/1978 | Matsuda et al. | |
| 4,090,980 A | 5/1978 | Carter et al. | |
| 4,166,805 A | 9/1979 | Jowett | |
| 4,229,361 A | 10/1980 | Cahen | |
| 5,039,649 A | 8/1991 | Lippert et al. | |

FOREIGN PATENT DOCUMENTS

| | | |
|---|---|---|
| EP | 0 446 481 B1 | 9/1991 |
| EP | 1 163 955 A1 | 12/2001 |
| GB | 1 475 689 | 6/1977 |
| GB | 2 246 307 A | 1/1992 |
| WO | WO 00/51733 | 9/2000 |

*Primary Examiner*—Brian Davis
(74) *Attorney, Agent, or Firm*—Ralph J. Mancini

(57) ABSTRACT

The invention relates to a passivated hydrogenation catalyst that is embedded in a primary amine, a derivative thereof, and/or a nitrile, the process to make such catalysts, as well as the use of such catalysts in a hydrogenation process in which an amine or a derivative thereof is produced.

20 Claims, No Drawings

IN AN AMINE OR NITRILE EMBEDDED PASSIVATED HYDROGENATION CATALYST

This application is a 371 of PCT/EP03/02637 filed Mar. 13, 2003.

The invention relates to a passivated hydrogenation catalyst embedded in an amine or nitrile.

Hydrogenation catalysts and their use to synthesise a wide variety of products are extensively documented. Active hydrogenation catalysts are difficult to handle. Therefore, they are typically treated before they are shipped/handled. For example, it is known (see commercial products of, e.g. Degussa, Engelhard, and Synetix) to embed active hydrogenation catalyst materials in dialkyl amines, such as Armeen® 2HT. These embedded catalysts are generally inexpensive and easy to handle. Also, it is known to passivate active hydrogenation catalysts, suitably by means of carbon monoxide and/or oxygen, to obtain a product that is easier to handle.

Active catalysts embedded in dialkyl amine are readily suitable for use in hydrogenation processes to make amines and/or derivatised amines. However, for the preparation of primary amines the use of catalysts embedded in dialkyl amines inherently means that the final primary amine or derivative thereof is contaminated with the dialkyl amine being introduced with the catalyst as embedding agent. Also, it was observed that such a contamination, particularly when making (unsaturated) primary amines, could result in hazy and/or cloudy products.

Passivated catalysts, on the other hand, also suffer from several drawbacks. First of all, passivation lowers the activity of the catalyst. Secondly, passivated hydrogenation catalysts, such as the commercially available Engelhard E-480P, are powdery materials that lead to undesired dusting (a health problem) and consequently are not easy to handle.

Hence, there is a need for improved hydrogenation catalysts that can be handled easily and without health risks and used in hydrogenation processes to make amines, particularly primary amines, especially unsaturated primary amines, from the corresponding nitrile precursor without the end product (i.e. primary amines or derivatives thereof) being contaminated with undesired material. By the term "corresponding nitrile precursor" is meant here that said nitrile, upon hydrogenation, produces the desired primary amine by just the addition of a certain amount of hydrogen to said nitrile, e.g. $R-C\equiv N+2H_2$ results in $R-CH_2-NH_2$.

Various routes to overcome the above-mentioned problems in a cost-effective way have been explored. Thus, many experiments were conducted to embed active hydrogenation catalysts in a primary amine. However, this route has not been successful,, since during the embedding process the primary amine embedding agent is converted into, inter alia, undesired secondary amine and undesired $NH_3$. After many years of research, we have now found that a passivated hydrogenation catalyst can be embedded in a primary amine, a derivative of said primary amine, or a (corresponding) nitrile. Surprisingly, this can be done in a cost-efficient way, without unacceptable loss of activity of the embedded passivated catalyst in the hydrogenation process, while the primary amines produced with said hydrogenation process i) are not contaminated with undesired products and said primary amines and/or derivatives thereof are obtainable by one or more subsequent derivation steps, and ii) are essentially free of any haze (using a test as described below). Consequently, distillation can be avoided, resulting in higher yields and a more cost-effective process.

Accordingly, this invention relates to passivated hydrogenation catalysts that are embedded in at least one embedding agent selected from the group consisting of
1) primary amines,
2) hydrocarbon moiety-substituted derivatives of said primary amines, wherein the hydrocarbon moiety may be linear or branched, saturated or unsaturated, substituted or unsubstituted, which if substituted may be O-containing and may be N-containing, preferably only N-containing,
3) nitriles, or
4) mixtures of any of these compounds.

Furthermore, this invention relates to the process to make said embedded catalysts and the use thereof in the hydrogenation process to make amines. Preferably, said hydrogenation process is the hydrogenation process of the corresponding nitrile precursor. More preferably, a primary amine or derivative thereof is produced in said hydrogenation process. The embedded passivated hydrogenation catalysts are pre-eminently suited for use in a hydrogenation process in which unsaturated primary amines or derivatives thereof are to be produced. The passivated hydrogenation catalyst may be present on a solid support material or it may be unsupported.

A hydrogenation catalyst as described in this description that is to be embedded can be any conventional hydrogenation catalyst known in the art. Preferred are hydrogenation catalysts selected from the group of supported or unsupported cobalt, nickel, copper, chromium, palladium, platinum, ruthenium, and zinc catalysts. Most preferred are hydrogenation catalysts that are pre-eminently suited for the hydrogenation of nitriles. Examples of catalysts which are very useful for the hydrogenation of nitrites include i) aluminum-nickel alloy, ii) Raney cobalt, iii) Raney nickel, iv) zinc-chromium alloy, v) zinc-aluminum alloy, vi) cobalt, copper, and/or chromium pellets, and vii) various nickel-supported materials. Preferred metals for use in a hydrogenation catalyst according to this invention are nickel, cobalt, and copper.

Preferred for use as embedding agent for the passivated hydrogenation catalyst are:
1) primary amines, represented by the formula $R-CH_2-NH_2$ (I), wherein R is selected from the group consisting of linear or branched, substituted or unsubstituted, saturated or unsaturated, optionally O-containing and optionally N-containing, preferably only N-containing, moieties containing 5 to 30 carbon atoms, preferably 6 to 30 carbon atoms, more preferably 7 to 30 carbon atoms, most preferably 8 to 30 carbon atoms,
2) derivatives of said primary amines, represented by the formula $R-CH_2-NR'R''$ (II), wherein R is as defined above and R' and R" are independently selected from hydrogen and the group consisting of linear or branched, substituted or unsubstituted, saturated or unsaturated, optionally O-containing and optionally N-containing, preferably only N-containing, moieties containing 3 to 30 carbon atoms, preferably 4 to 30 carbon atoms, more preferably 5 to 30 carbon atoms, most preferably 6 to 30 carbon atoms, with the proviso that at most one of R' and R" is hydrogen and with the further proviso that $R-CH_2-NR'R''$ is not a difatty secondary amine, wherein the term "fatty" refers to a moiety having 10 or more carbon atoms,
3) nitrites, represented by the formula $R-C\equiv N$ (III), wherein R is as defined above, and
4) mixtures of any of said primary amines, derivatives thereof, and nitrites.

The ratio of passivated hydrogenation catalyst to embedding agent is preferably 10–60% by weight (wt. %) of said catalyst to 40–90 wt. % of embedding agent, up to a total of 100%, based on the combined weight of hydrogenation catalyst and embedding agent. More preferably, the ratio is 35–40 wt. % of catalyst to 60–65 wt. % of embedding agent. Optionally, the embedded passivated hydrogenation catalyst may comprise further conventional additives, such as filter aids, in a ratio by weight of 1:10–10:1 (embedded passivated hydrogenation catalyst:total amount of further additives).

Preferred embedding agents are selected from:
- alkyl amines (Armeen®), n-butyl amine, n-hexyl amine, n-octyl amine, n-decyl amine, n-dodecyl amine, n-butadecyl amine, n-hexadecyl amine, n-octadecyl amine, n-eicosanyl amine, n-docosanyl amine, and mixtures thereof, such as commercially available tallow, hydrogenated tallow, palm, palm kernel, coco-, oleyl, or erucic amines,
- nitriles, such as n-butyronitrile, n-hexane nitrile, n-octane nitrile, n-decane nitrile, n-dodecane nitrile, and mixtures thereof, such as commercially available tallow, hydrogenated tallow, palm, palm kernel, coco-, soya, rape, erucic, or oleyl nitriles,
- dialkyl amines (Armeen®) having at most one fatty alkyl group, wherein the term "fatty" refers to a moiety having 10 or more carbon atoms, preferably dialkyl amines wherein both alkyl groups have less than 10 carbon atoms, such as di(n-butyl) amine, di(n-hexyl) amine, di(n-octyl)amine,
- trialkyl amines, including dimethyl alkyl amines and methyl dialkyl amines (Armeen®)), such as commercially available hexadecyl dimethyl amine, cocodimethyl amine, hydrogenated tallow dimethyl amine, oleyl dimethyl amine, tallow dimethyl amine, didecyl methyl amine, dicocomethyl amine, di(hydrogenated tallow) methyl amine,
- 1,3-diaminopropane amines (Duomeen®), such as commercially available cocopropylene diamine, (hydrogenated) tallow propylene diamine, oleyl propylene diamine, $C_{16}$–$C_{22}$-alkyl propylene diamine,
- alkyl dipropylene triamine (Triameen®), including (Triameen® Y), such as commercially available cocodipropylene triamine, (hydrogenated) tallow dipropylene triamine, oleyl dipropylene triamine, tallow dipropylene triamine,
- alkyl tripropylene tetramine (Tetrameen®), such as commercially available cocotripropylene tetramine, (hydrogenated) tallow tripropylene tetramine, oleyl tripropylene tetramine,
- trimethylalkyl-1,3-diaminopropane,
- ether amines,
- ether diamines, and
- mixtures of any of the above compounds.

Preferably, a primary amine and/or a corresponding nitrile are/is used as embedding agent. Also mixtures of one or more primary amines with one or more of the corresponding nitriles can be used. Preferably, at least 40% by weight, more preferably at least 80% by weight, most preferably at least 95% by weight of the embedding agent consists of one or more products according to the formulae (I), (II), and (III). Amines, derivatives thereof, or nitriles according to this description can be based on natural or synthetic raw material (fats/oils, alcohols). At room temperature and atmospheric pressure, said amine, derivative thereof, or nitrile preferably has a vapour pressure below 5 mm Hg, so that it is not volatile. The amine, derivative thereof, or nitrile can be liquid or solid, at room temperature and atmospheric pressure, although solid embedding agents are preferred. If an amine is used as the embedding material and the hydrogenation catalyst is used in the process to make amines, then it is preferred to use as the embedding material the same amine as the amine that is to be produced during the hydrogenation process. Similarly, if a nitrile is used as the embedding material, then it is preferably the nitrile that is hydrogenated in the process to make the amine.

Examples of amines and derivatives thereof that can be prepared using the embedded passivated hydrogenation catalysts according to the invention include:
- alkyl amines (Armeen®)),
- ethoxylated alkyl amines (Ethomeen®),
- dialkyl amines (Armeen®),
- trialkyl amines, including dimethyl alkyl amines and methyl dialkyl amines (Armeen®),
- 1,3-diaminopropane amines (Duomeen®),
- ethoxylated 1,3-diaminopropane amines (Ethoduomeen®),
- alkyl dipropylene triamine (Triameen®, including Triameen®Y),
- alkyl tripropylene tetramine (Tetrameen®),
- quaternary ammonium compounds, including alkyl trimethyl, dialkyl dimethyl, alkyl benzyl dimethyl, dialkyl benzyl methyl compounds (Arquad®),
- trimethylalkyl-1,3-diaminopropane,
- a pentamethylalkyl-1,3-propane diammonium compounds (sold as Duoquad®),
- ethoxylated quaternary ammonium compounds, such as alkylmethyl-bis(2-hydroxylethyl)ammonium compounds (Ethoquad® X/12),
- polyoxyethylene alkyl methyl ammonium compounds, such as Berol® 556, Berol® 561, and Berol® 563 and Ethoquad®,
- amine salts (Armac®),
- diamine salts (Duomac®),
- amine oxides (based on dimethyl alkyl amines or ethoxylated amines, Aromox®),
- amphoterics, such as N-alkyl-3-aminobutyric acid (Armeen® Z),
- ether amines,
- ether diamines,
- reaction products of SMCA (sodium salt of monochloroacetic acid) and alkyl dimethyl amines (Amphoteen®),
- reaction products of SMCA and alkyl diaminopropane, Triameen®, and/or Tetrameen® (sold as Ampholak®), and
- mixtures of any of the above compounds.

Preferably, the amine produced in the hydrogenation process in which the embedded catalyst according to the invention is used, is a primary amine or a derivative thereof. Most preferably, the amine produced is an unsaturated primary amine or a derivative thereof, since it was observed that the present embedded catalyst shows good performance, resulting in higher purity of the resulting primary amine, absence of clarity problems, and higher yields, because distillation is no longer required. High yields are even obtained when distillation of the reaction product is still applied. Nonetheless, in a preferred hydrogenation process wherein the embedded catalyst according to the invention is used, the resulting primary amine is not distilled.

In a typical hydrogenation process wherein a metal-containing hydrogenation catalyst according to this invention is used, the amount of metal in the hydrogenation catalyst preferably is from 0.02 to 1.0 wt. %, based on the weight of the compound to be hydrogenated. More preferably, the amount of metal is from 0.05 to 0.25 wt. %.

The invention is elucidated by the following examples, which have not been optimised.

EXPERIMENTAL

Test procedure for determining haze:
Filter 5 ml of an amine sample using a Millipore 0.45 μm filter unit, type Millex HV
Collect the filtrate in a 10 ml vial
Rinse with $N_2$-blanket and capsulate the vial using a rubber septum
Place the vial in an oil bath at 105° C.
Remove the vial from the heating source after 30 minutes
Allow the vial to cool in an ice bath for 2 hours
Place the vial in a thermostatic water bath at 20° C. (t=0)
Check the sample for appearance after 30 minutes
Increase the temperature to 21° C.
Check the sample for appearance after 15 minutes
Increase the temperature to 22° C.
Check for appearance after 15 minutes, and increase the temperature by 1° C.
Repeat the previous step until the sample is completely clear (maximum temperature 30° C.)
Register the temperature at which the sample is completely clear without any sediment

| Materials used: | |
|---|---|
| E-480P | A nickel-containing catalyst ex Calsicat/Mallinckrodt* |
| 62/15P | A nickel-containing catalyst ex Synetix |
| Armeen ® HT | Embedding agent ex Akzo Nobel |

*Calsicat/Mallinckrodt now belongs to Engelhard

Example 1

Preparation of an Embedded Passivated Hydrogenation Catalyst

Equipment:
The embedded catalyst can be produced and shaped in any conventional way. In this example, a thermostatted, glass lined reactor (250 ml), equipped with a turbine mixer, a nitrogen supply in the headspace, and a bottom valve was used. The embedded catalyst mixture produced herein, see below, was dropped from the bottom valve onto a metal plate situated on carbon dioxide ice for cooling, to form particulate matter.

Procedure:
60 g Armeen® HT were melted at a temperature of approx. 70° C., and the reactor was flushed with nitrogen. Next, 40 grams of catalyst E-480P were added to the reactor and mixed into the melted Armeen® HT. While maintaining a nitrogen blanket, and optionally using nitrogen to pressurise the reactor, the mixture was shaped as described above. The Ni content of the embedded catalyst material was about 25 wt. %, based on the total combined weight of Armeen® HT and E-480P.

Examples 2–3

Hydrogenation Experiments
The experiments were carried out using a conventional hydrogenation process as described in the open literature for the preparation of primary amines from nitriles. Oleyl nitrile was used as the raw material to be hydrogenated.

| | | Example | |
|---|---|---|---|
| | | 2 | 3 |
| Passivated catalyst | | E-480P | 62/15P |
| Embedding agent | | Armeen ® HT | Armeen ® HT |
| (Emb. agent + Passivated cat.)/Ni [wt. %]* | | 0.8/0.2 | 2.4/0.2 |

*Based on the weight of the compound to be hydrogenated

An oleyl amine with the following properties was obtained:

| Primary Amine | [wt. %]** | 97.6 | 97.1 |
|---|---|---|---|
| Secondary Amine | [wt. %]** | 2.4 | 2.9 |
| IV | [g $I_2$/100 g] | 86 | 86 |
| Time | [min.] | 180 | 160 |
| Minimum Clarity temperature | [° C.] | 21 | 23 |

**Normalised
IV = Iodine Value is the standard measure for the degree of unsaturation of the product.

From these results it can be concluded that passivated hydrogenation catalyst can be embedded perfectly in primary amine (Armeen® HT). Also good yields and desirable products are obtained in the hydrogenation process in which this catalyst is used.

The invention claimed is:

1. A pasaivated hydrogenation catalyst that is embedded in at least one embedding agent selected from the group consisting of:
   primary amines, represented by the formula R—$CH_2$—$NH_2$ (I), wherein R is selected from the group consisting of linear or branched, substituted or unsubstituted, saturated or unsaturated, optionally O-containing and optionally N-moieties containing 7 to 30 carbon atoms,
   derivatives of said primary amines, represented by the formula R—$CH_2$—NR'R" (II), wherein R is as defined above and R' and R" are independently selected from hydrogen and the group consisting of linear or branched, substituted or unsubstituted, saturated or unsaturated, optionally O-containing and optionally N-containing moieties containing 3 to 30 carbon atoms, with the proviso that at most one of R' and R" is hydrogen,
   nitriles, represented by the formula R—C≡N (III), wherein R is selected from the group consisting of linear or branched, substituted or unsubstituted, saturated or unsaturated, optionally O-containing and optionally N-containing moieties containing 7 to 30 carbon atoms,
   ether amines,
   ether diamines, and
   mixtures of any of said primary amines, derivatives thereof, nitrites, ether amines, and ether diamines.

2. A catalyst according to claim 1 wherein at least one of the embedding agents is solid at room temperature and atmospheric pressure.

3. A catalyst according to claim 2 wherein the combined amount of embedding agent is solid at room temperature and atmospheric pressure.

4. A hydrogenation process wherein an amine is produced using a catalyst in accordance with claim 1.

5. A process according to claim 4 wherein the amine produced is a primary amine.

6. A process according to claim 5 wherein the primary amine is an unsaturated primary amine.

7. A process according to claim 4 wherein the embedding agent used is the same as the nitrile that is hydrogenated.

8. A process according to claim 4 wherein the embedding agent used is the same as the amine produced, or a derivative thereof.

9. A process to make a catalyst according to ciaim 1 wherein a passivated hydrogenation catalyst is embedded in at least one embedding agent selected from the group consisting of primary amines, represented by the formula R—$CH_2$—$NH_2$ (I), wherein R is selected from the group consisting of linear or branched, substituted or unsubstituted saturated or unsaturated, optionally O-containing and optionally N-containing moieties 7 to 30 carbon atoms, derivatives of said primary amines, represented by the formula R—$CH_2$—NR'R" (II), wherein R is as defined above and R' and R" are independently selected from hydrogen and the group consisting of linear or branched, substituted or unsubstituted, saturated or unsaturated, optionally O-containing and optionally N-containing mioieties containing 3 to 30 carbon atoms, with the proviso that at most one of R' and R" is hydrogen, nitriles, represented by the formula R—C≡N (III), wherein R is selected from the group consisting of linear or branched, substituted or unsubstituted, saturated or unsaturated, optionally O-containing and optionally N-contalning moieties containing 5 to 30 carbon atoms, ether emines, ether dlamines, and mixtures of any of said primary amines, derivatives thereof nitriles, ether amines, and ether diamines.

10. A process according to claim 4 wherein the ratio of passivated hydrogenation catalyst and embedding agent is 10–60% by weight (wt. %) of said catalyst to 40–90wt .% of embedding agent, up to a total of 100%, based on the combined weight of hydrogenation catalyst and embedding agent, while the embedded pessivated hydrogenation catalyst may comprise further conventional additives.

11. The passivated hydrogenation catalyst of claim 1 wherein said embedding agent is a primary amine represented by the formula R—$CH_2$—$NH_2$ (I), wherein R is selected from the group consisting of linear or branched, substituted or unsubstituted, saturated or unsaturated optionally N-containing moiety containing 7 to 30 carbon atom.

12. The passivated hydrogenation catalyst of claim 1 wherein said embedding agent is a derivative of a primary amine represented by the formula R—$CH_2$—NR'R" (II), wherein R is as defined above and R' and R" are independently selected from hydrogen and the group consisting of linear or branched, substituted or unsubstituted, saturated or unsaturated, optionally N-containing moiety containing 3 to 30 carbon atoms.

13. The passivated hydrogenation catalyst of claim 12 wherein said N-containing moiety contains 5 to 30 carbon atoms.

14. The passivated hydrogenation catalyst of claim 12 wherein said N-containing moiety contain 6 to 30 carbon atoms.

15. The passivated hydrogenation catalyst of claim 1 wherein said embedding agent is a nitrile represented by the formula R—C≡N (III), wherein R is selected from the group consisting of linear or branched substituted or unsubstituted, saturated or unsaturated, optionally N-containing moiety containing 5 to 30 carbon atoms.

16. The passivated hydrogenation catalyst of claim 15 wherein said N-containing moiety contains 7 to 30 carbon atoms.

17. The passivated hydrogenation catalyst of claim 15 wherein said N-containing moiety contains 8 to 30 carbon atoms.

18. The process of claim 9 wherein the at least one embedding agent is a primary amine represented by the formula R—$CH_2$—$NH_2$ (I), wherein R is selected from the group consisting of linear or branched, substituted or unsubstituted, saturated or unsaturated optionally N-containing moiety containing 7 to 30 carbon atoms.

19. The process of claim 9 wherein said embedding agent is a derivative of a primary amine represented by the formula R—$CH_2$—NR'R" (II), wherein R is as defined above and R' and R" are independently selected from hydrogen and the group consisting of linear or branched, substituted or unsubstituted, saturated or unsaturated, optionally N-containing moiety containing 5 to 30 carbon atoms.

20. The process of claim 9 wherein said embedding agent is a nitrile represented by the formula R—C≡N (III), wherein R is selected from the group consisting of linear or branched, substituted or unsubstituted, saturated or unsaturated, optionally N-containing moiety containing 7 to 30 carbon atoms.

* * * * *

UNITED STATES PATENT AND TRADEMARK OFFICE
CERTIFICATE OF CORRECTION

PATENT NO. : 7,208,448 B2  Page 1 of 1
APPLICATION NO. : 10/505661
DATED : April 24, 2007
INVENTOR(S) : Thale Jacob Ottens, Jacobus Van Den Berg and Paul Van Poecke It is certified that error appears in the above-identified patent and that said Letters Patent is hereby corrected as shown below:

Col. 6, Line 33,   change "pasaivated" to --passivated--

Col. 6, Line 59,   change "nitrites" to --nitriles--

Signed and Sealed this

Twenty Second Day of April, 2008

JON W. DUDAS
*Director of the United States Patent and Trademark Office*